United States Patent
Hishinuma et al.

(10) Patent No.: US 8,075,105 B2
(45) Date of Patent: Dec. 13, 2011

(54) PEROVSKITE-TYPE OXIDE FILM, PIEZOELECTRIC THIN-FILM DEVICE AND LIQUID EJECTING DEVICE USING PEROVSKITE-TYPE OXIDE FILM, AS WELL AS PRODUCTION PROCESS AND EVALUATION METHOD FOR PEROVSKITE-TYPE OXIDE FILM

(75) Inventors: Yoshikazu Hishinuma, Kanagawa (JP); Takamichi Fujii, Kanagawa (JP); Takayuki Naono, Kanagawa (JP); Yuuichi Okamoto, Kanagawa (JP); Ryosuke Ozawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 312 days.

(21) Appl. No.: 12/560,131

(22) Filed: Sep. 15, 2009

(65) Prior Publication Data

US 2010/0066788 A1   Mar. 18, 2010

(30) Foreign Application Priority Data

Sep. 16, 2008 (JP) ................... 2008-236636

(51) Int. Cl.
- *B41J 2/045* (2006.01)
- *C04B 35/495* (2006.01)
- *C04B 35/00* (2006.01)
- *H01L 41/18* (2006.01)
- *H01L 41/187* (2006.01)

(52) U.S. Cl. ............... 347/68; 252/62.9 R; 252/62.9 PZ

(58) Field of Classification Search ............... 347/68, 347/70–72; 310/311, 321; 252/62.9 R, 62.9 PZ
See application file for complete search history.

(56) References Cited

U.S. PATENT DOCUMENTS

| | | |
|---|---|---|
| 2006/0046319 A1 | 3/2006 | Takeda |
| 2007/0138906 A1 | 6/2007 | Tsukamoto |
| 2008/0012908 A1 | 1/2008 | Takeda et al. |

FOREIGN PATENT DOCUMENTS

| | | |
|---|---|---|
| JP | 2002-094023 A | 3/2002 |
| JP | 2005-253274 A | 9/2005 |
| JP | 2005-350735 A | 12/2005 |
| JP | 2007-116091 A | 5/2007 |
| JP | 2007-173400 A | 7/2007 |
| JP | 2007-258389 A | 10/2007 |
| JP | 2008-42192 A | 2/2008 |
| WO | WO-2007/034903 A1 | 3/2007 |

*Primary Examiner* — Matthew Luu
*Assistant Examiner* — Lisa Solomon
(74) *Attorney, Agent, or Firm* — Birch, Stewart, Kolasch & Birch, LLP

(57) ABSTRACT

Provided is a perovskite-type oxide film having a perovskite-type crystal structure and containing lead as a chief component, which, when subjected to Raman microspectroscopy at a plurality of points on a surface thereof so as to measure Raman spectra upon application of an electric field of 100 kV/cm and upon application of no electric field, has a mean of absolute values of peak shift amounts that is 2.2 cm$^{-1}$ or less, with the peak shift amounts being found between Raman spectra in a range of 500 to 650 cm$^{-1}$ measured upon application of an electric field of 100 kV/cm and Raman spectra in the range of 500 to 650 cm$^{-1}$ measured upon application of no electric field. A production process and an evaluation method for such a film as well as a device using such a film are also provided.

15 Claims, 2 Drawing Sheets

PEROVSKITE-TYPE OXIDE FILM, PIEZOELECTRIC THIN-FILM DEVICE AND LIQUID EJECTING DEVICE USING PEROVSKITE-TYPE OXIDE FILM, AS WELL AS PRODUCTION PROCESS AND EVALUATION METHOD FOR PEROVSKITE-TYPE OXIDE FILM

The entire contents of the documents cited in this specification are incorporated herein by reference.

BACKGROUND OF THE INVENTION

The present invention relates to perovskite-type oxide films, production processes and evaluation methods for such films, as well as devices using such films.

In recent years, research and development have been conducted actively on a variety of devices such as actuators, sensors and memory devices for which piezoelectric materials are used, whereupon piezoelectric films deposited by a vapor-phase deposition technique such as sputtering receive attention as high-performance, functional films. The piezoelectric films are used as a piezoelectric thin-film device for a piezoelectric actuator in an inkjet recording head (liquid ejecting device), a micropump, and so forth, of which a high piezoelectric performance is required.

At present, the piezoelectric thin-film device is decreased in displacing capability upon application of an electric field thereto, that is to say, deteriorated, as it is exposed to a higher relative humidity and temperature.

Specifically, a problem lies in that the moisture around a piezoelectric film increases a leakage current to cause dielectric breakdown or promotes ion migration by making a constituent of the piezoelectric film ionized.

Measures against heat and humidity are accordingly critical to the piezoelectric films of which a high piezoelectric performance is required, and also indispensable from the viewpoint of the durability of a device using a piezoelectric film.

For the purpose of increasing device durability, US 2006/0046319 A1, for instance, proposes distribution of the mean stress received by a piezoelectric film by providing a stress-relieving layer which is formed by orientational film deposition or epitaxial film deposition.

In JP 2005-253274 A, it is disclosed that a stress-relieving section for relieving the stress on a piezoelectric device is provided by cutting a slit in an electrode layer.

Such a stress-relieving layer or stress-relieving section as described in US 2006/0046319 A1 or JP 2005-253274 A, however, will be provided at the expense of much time and effort, and increase the fabrication costs.

Moreover, it is not possible with the conventional measures to fully relieve the stress generated in a piezoelectric film during the application of a voltage thereto so as to attain a satisfactory device durability. One reason for this is that, while deterioration is liable to begin where stress is localized, a localized stress cannot be removed by providing the stress-relieving layer or stress-relieving section.

SUMMARY OF THE INVENTION

It is therefore an object of the present invention to solve the above problems involved with the prior art and provide a perovskite-type oxide film which serves as a piezoelectric film capable of relieving the stress localized during the application of a voltage to the film.

Another object of the present invention is to provide a piezoelectric thin-film device and a liquid ejecting device each using such a perovskite-type oxide film.

It is also an object of the present invention to provide a production process and an evaluation method for such a perovskite-type oxide film.

A perovskite-type oxide film according to the present invention has a perovskite-type crystal structure and containing lead as a chief component, which, when subjected to Raman microspectroscopy at a plurality of points on a surface thereof so as to measure Raman spectra upon application of an electric field of 100 kV/cm and upon application of no electric field, has a mean of absolute values of peak shift amounts that is 2.2 cm$^{-1}$ or less, with the peak shift amounts being found between Raman spectra in a range of 500 to 650 cm$^{-1}$ measured upon application of an electric field of 100 kV/cm and Raman spectra in the range of 500 to 650 cm$^{-1}$ measured upon application of no electric field.

A piezoelectric thin-film device according to the present invention comprises: a piezoelectric film composed of such a perovskite-type oxide film; and a lower electrode and an upper electrode formed on two surfaces of the piezoelectric film, respectively, to apply a voltage to the piezoelectric film.

A liquid ejection unit according to the present invention comprises: a liquid storing/ejecting member provided with a liquid reservoir for storing liquid and a liquid ejecting port connecting the liquid reservoir with outside; and the above-described piezoelectric thin-film device which is so arranged as to face the liquid reservoir.

A process for producing a perovskite-type oxide film according to the present invention comprises the steps of: depositing a perovskite-type oxide film having a perovskeite-type crystal structure and containing lead as a chief component by sputtering; annealing the oxide film deposited at a specified temperature for a specified period of time; subjecting the oxide film after annealing to Raman microspectroscopy at a plurality of points on a surface thereof so as to measure Raman spectra upon application of an electric field of 100 kV/cm and upon application of no electric field; finding conditions under which a mean of absolute values of peak shift amounts is 2.2 cm$^{-1}$ or less, with the peak shift amounts being found between Raman spectra in a range of 500 to 650 cm$^{-1}$ measured upon application of an electric field of 100 kV/cm and Raman spectra in the range of 500 to 650 cm$^{-1}$ measured upon application of no electric field; and producing the perovskite-type oxide film under the conditions found.

A method of evaluating a perovskite-type oxide film according to the present invention comprises the steps of: subjecting a perovskite-type oxide film having a perovskeite-type crystal structure and containing lead as a chief component to Raman microspectroscopy at a plurality of points thereon so as to measure Raman spectra upon application of an electric field of 100 kV/cm and upon application of no electric field; determining whether or not a mean of absolute values of peak shift amounts is 2.2 cm$^{-1}$ or less, with the peak shift amounts being found between Raman spectra in a range of 500 to 650 cm$^{-1}$ measured upon application of an electric field of 100 kV/cm and Raman spectra in the range of 500 to 650 cm$^{-1}$ measured upon application of no electric field; and evaluating the perovskite-type oxide film as capable of relieving stress localized during application of an electric field to the film if the mean of the absolute values of the peak shift amounts is 2.2 cm$^{-1}$ or less.

DETAILED DESCRIPTION OF THE INVENTION

On the following pages, the present invention is described in detail with reference to a preferred embodiment as shown in the accompanying drawings.

Figure 1:
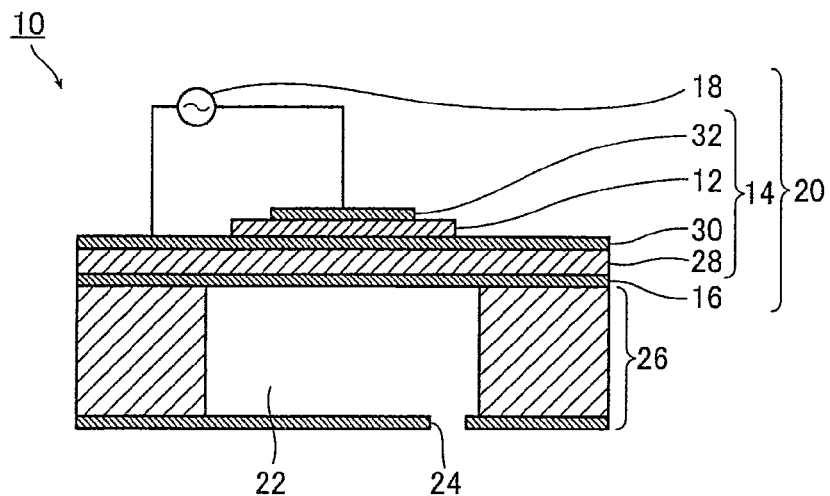
FIG. 1 is a schematic cross-sectional view illustrating the structure of an inkjet recording head using a piezoelectric film according to an embodiment of the present invention.

FIG. 1 illustrates the structure of an inkjet recording head (liquid ejecting device) 10 using a piezoelectric film 12 according to an embodiment of the present invention.

The inkjet recording head 10 comprises a piezoelectric actuator 20 of the diaphragm type and an ink nozzle member (liquid storing/ejecting member) 26 on which the piezoelectric actuator 20 is mounted.

The piezoelectric actuator 20 has a piezoelectric thin-film device 14 in which the piezoelectric film 12 is used, a diaphragm 16 which vibrates in response to the expansion and contraction of the piezoelectric film 12, and a control means 18 for controlling the driving of the piezoelectric thin-film device 14.

The ink nozzle member 26 is provided with an ink compartment (liquid reservoir) 22 for storing ink, the ink compartment 22 being covered on one side with the diaphragm 16 of the piezoelectric actuator 20 and having an ink ejecting port (liquid ejecting port) 24 formed on the opposite side, through which the compartment 22 communicates with the outside.

The piezoelectric film 12 is an oxide film containing lead as a chief component and having a perovskite-type crystal structure. To be more specific, the piezoelectric film 12 is a perovskite-type oxide film which, when subjected to Raman microspectroscopy at a plurality of points on a surface thereof so as to measure Raman spectra upon application of an electric field of 100 kV/cm and upon application of no electric field, has the mean of absolute values of peak shift amounts that is 2.2 cm$^{-1}$ or less, with the peak shift amounts being found between the Raman spectra in the range of 500 to 650 cm$^{-1}$ measured upon application of an electric field of 100 kV/cm and the Raman spectra in the range of 500 to 650 cm$^{-1}$ measured upon application of no electric field.

It should be noted that, by performing Raman microspectroscopy on the piezoelectric film 12 with and without an electric field applied thereto to measure two Raman spectra and find the peak shift amount between them, the stress generated in the piezoelectric film 12 during the application of an electric field thereto can be estimated. If the peak shift amount is larger in absolute value, a larger stress should be generated in the piezoelectric film 12, and vice versa.

In order to prevent an erroneous determination due to the variation in peak shift amount with measuring position on the surface of the piezoelectric film 12, measurement is preferably carried out at about 20 points.

The perovskite-type oxide film in which the mean of the absolute values of the peak shift amounts is 2.2 cm$^{-1}$ or less is effective at minimizing the deterioration of a piezoelectric film at high temperature and relative humidity to increase the device durability.

The perovskite-type oxide film as the piezoelectric film 12 is not particularly limited in composition as long as it possesses the characteristics as stated above.

Preferably, the piezoelectric film 12 is composed of one or more perovskite-type oxides represented by the following general formula (P):

$$ABO_3 \qquad\qquad (P)$$

[where A is elemental lead (Pb) as an element at site A,

B is at least one element selected as an element at site B from the group consisting of Ti, Zr, V, Nb, Ta, Cr, Mo, W, Mn, Mg, Sc, Co, Cu, In, Sn, Ga, Zn, Cd, Fe, Ni, Hf, and Al, and O is elemental oxygen; and where the molar ratio between the element at site A and the element or elements at site B and the elemental oxygen, which is typically 1:1:3, may vary within the range enabling a perovskite structure].

Examples of the perovskite-type oxide represented by general formula (P) include lead-containing compounds such as lead titanate, lead zirconate titanate (PZT), lead zirconate, lead lanthanum titanate, lead lanthanum zirconate titanate, lead magnesium niobate-lead zirconate titanate, lead nickel niobate-lead zirconate titanate and lead zinc niobate-lead zirconate titanate, as well as mixtures thereof.

Since electrical properties are improved, it is preferable that the perovskite-type oxide further contains at least one metallic element selected from the group consisting of niobium (Nb), bismuth (Bi), strontium (Sr), barium (Ba), calcium (Ca), and lanthanum (La)(or lanthanoids (La, Ce, Pr, Nd, Sm, Eu, Gd, Tb, Dy, Ho, Er, Tm, Yb and Lu)).

The piezoelectric film 12 may be produced by a process including a preliminary step of subjecting a perovskite-type oxide film having a perovskite-type crystal structure and containing lead as a chief component to Raman microspectroscopy at a plurality of points on a surface thereof so as to measure Raman spectra upon application of an electric field of 100 kV/cm and upon application of no electric field, and finding the conditions under which the mean of absolute values of peak shift amounts is 2.2 cm$^{-1}$ or less, with the peak shift amounts being found between Raman spectra in the range of 500 to 650 cm$^{-1}$ measured upon application of an electric field of 100 kV/cm and Raman spectra in the range of 500 to 650 cm$^{-1}$ measured upon application of no electric field. In that case, a perovskite-type oxide film is produced as the piezoelectric film 12 under the conditions found. The present invention, however, is in no way limited to this.

It is also possible to form a plurality of perovskite-type oxide films having a perovskite-type crystal structure and containing lead as a chief component, and select from among them the oxide film in which the mean of the absolute values of the peak shift amounts as above is 2.2 cm$^{-1}$ or less.

The film deposition technique to be used is not particularly limited as long as the above perovskite-type oxide film having a perovskite-type crystal structure and containing lead as a chief component can be deposited, with a vapor-phase deposition technique such as sputtering being preferred. Conditions for film deposition, such as film deposition temperature or gas pressure, are not particularly limited either as long as the above perovskite-type oxide film having a perovskite-type crystal structure and containing lead as a chief component can be deposited.

Preferably, the mean of the absolute values of the peak shift amounts as above is used for durability evaluation, and the perovskite-type oxide film is produced which is evaluated as durable.

The perovskite-type oxide film of the present invention is preferably annealed after being deposited by a vapor-phase deposition technique such as sputtering.

For the annealing, a temperature of 150 to 500° C. and a duration of two to ten hours are preferred.

The piezoelectric thin-film device 14 is a device having a substrate 28 on which a lower electrode 30, the piezoelectric film 12, and an upper electrode 32 are superposed in this order. The lower electrode 30 and the upper electrode 32 are adapted to apply an electric field to the piezoelectric film 12 in the direction of its thickness.

Examples of the material for the substrate 28 include silicon, glass, stainless steel (JIS classification: SUS series), yttria-stabilized zirconia (YSZ), alumina, sapphire, SiC, and $SrTiO_3$. It is also possible to use a laminated substrate, such as an SOI substrate composed of the silicon substrate on which a $SiO_2$ film and an active Si layer are sequentially formed, as the substrate 28.

The material to be used in the lower electrode 30 as a chief component is exemplified by such metals and metal oxides as gold (Au), platinum (Pt), iridium (Ir), iridium oxide ($IrO_2$), ruthenium oxide ($RuO_2$), $LaNiO_3$ and $SrRuO_3$, as well as combinations thereof.

The material to be used in the upper electrode 32 as a chief component is exemplified by, apart from the above materials for the lower electrode 30, electrode materials commonly used in the semiconductor process, such as aluminum (Al), tantalum (Ta), chromium (Cr) and copper (Cu), as well as combinations thereof.

The lower and upper electrodes 30 and 32 are preferably of a thickness of 50 to 500 nm each.

It is preferable that the piezoelectric film 12 of the piezoelectric thin-film device 14, as being a lead-containing thin film, has a lead concentration near the interface with the lower electrode 30 which is equal to or higher than the mean lead concentration of the piezoelectric film 12 as a whole. If that is the case, the piezoelectric film 12 will have a perovskite structure free of heterophases such as a lead oxide or pyrochlore phase.

In this connection, the phrase "near the interface with the lower electrode 30" is to be construed as "about 100 nm away from the surface of the piezoelectric film 12 that is in contact with the lower electrode 30."

The piezoelectric actuator 20 has such a configuration that the diaphragm 16 is attached to the back side of the substrate 28 of the piezoelectric thin-film device 14. In addition, the piezoelectric actuator 20 includes a driving circuit or the like as the control means 18 for controlling the driving of the piezoelectric thin-film device 14.

In the inkjet recording head 10, the ink nozzle member 26 provided with the ink compartment 22 and the ink ejecting port 24 connecting the compartment 22 with the outside is arranged underneath the piezoelectric actuator 20.

During the operation of the inkjet recording head 10, the piezoelectric thin-film device 14 is expanded or contracted by modifying the intensity of the electric fields applied to the device 14 so as to control ink ejection from the ink compartment 22 in timing and amount.

While the substrate 28, the diaphragm 16 and the ink nozzle member 26 are formed as discrete layers in the embodiment as described above, the substrate 28 may partially be processed into the diaphragm 16 and the ink nozzle member 26.

In an exemplary case where the substrate 28 is composed of a laminated substrate such as an SOI substrate, it is possible to form the ink compartment 22 by etching the substrate 28 from the back side, and provide the diaphragm 16 and the ink nozzle member 26 by processing the substrate in itself.

In the embodiment as above, the piezoelectric film of the present invention is used in a piezoelectric actuator of an inkjet recording head, although the present invention is not limited to this embodiment. The present invention is applicable to a variety of devices for which a piezoelectric actuator can be employed, such as a micropump and a surface acoustic-wave device.

EXAMPLES

The present invention is specifically explained by the following Examples, which in no way limit the present invention.

In the Examples, the piezoelectric films and piezoelectric thin-film devices prepared were identical in configuration to those in the inkjet recording head 10 as described above.

Example 1

[Raman Microspectroscopy]

On a Si substrate 28 with a thickness of 500 μm, a 20 nm thick titanium (Ti) layer and a 100 nm thick platinum (Pt) layer were sequentially formed by sputtering to provide a lower electrode 30. Then on the lower electrode 30, a lead zirconate titanate (PZT) film (piezoelectric film) 12 with a thickness of 4.0 μm was deposited by sputtering. Two specimens were prepared, one by slowly decreasing the temperature in the sputtering apparatus to anneal the deposited film at 300° C. for five hours (specimen A) and the other with no annealing (specimen B).

The sputtering apparatus used was the model MPS-3000 from ULVAC, Inc., and the target was a PZT target (composition: $Pb_{1.3}(Zr_{0.52}Ti_{0.48})O_3$). The PZT film (piezoelectric film) 12 was deposited under such conditions that the total pressure was 0.5 Pa, the gas for film deposition consisted of 99% Ar and 1% $O_2$, the film deposition temperature was 500° C., and the RF power was 500 W.

On the PZT film 12 of each of specimens A and B, a 20 nm thick titanium (Ti) layer and a 100 nm thick platinum (Pt) layer were sequentially formed by sputtering so as to provide a patterned upper electrode 32. The upper electrode 32 had a 300×800 μm rectangular pattern, with the corners being rounded in order to avoid the concentration of electric fields.

The two specimens (PZT films) prepared as above were subjected to Raman microspectroscopy to measure local strains thereon.

The microscopic Raman instrument used was the model in Via Reflex from Renishaw plc (excitation at 532 nm; 3 mW; 50× magnification lens), with the measurement wave number having ranged from 120 $cm^{-1}$ to 700 $cm^{-1}$.

An electric field of 100 kV/cm was applied to each of specimens A and B, and the PZT film 12 of the relevant specimen was subjected to Raman microspectroscopy in an exposed part of its surface at the points which were each within 3 μm of the boundary between the upper electrode 32 and the PZT film 12. This measurement on the surface of the PZT film 12 was performed at about 20 points, and observations were made on the wave number shift in the range of 500 to 650 $cm^{-1}$, in which Raman peak shifts due to stress are assumed as remarkable. Vibration at a wave number in this range is a vibration in mode $A_1$ (3 TO) where the Pb in the above general formula (P) as the site A ion and the Ti and Zr as the site B ions vibrate 180° out of phase with each other, namely, a lattice vibration sensitive to stress (Manoj K. Singh, Sangwoo Ryu, and Hyun M. Jang, Phys. Rev. B 72, 132101 (2005)).

Application of electric fields was carried out by bringing a probe into contact with the upper and lower electrodes 32 and 30.

For the purpose of confirming the stress localization during the application of an electric field, another specimen (specimen C) was prepared without annealing of the deposited film, as is the case with specimen B. An electric field of 100 kV/cm was applied to specimen C, and the PZT film 12 of the specimen was subjected to Raman microspectroscopy in an exposed part of its surface at the points which were each 20 μm away from the boundary between the upper electrode 32 and the PZT film 12. The measurement on the surface of the PZT film 12 was performed at about 20 points, and observations were made on the wave number shift in the range of 500 to 650 cm$^{-1}$.

In addition, for the purpose of demonstrating the generation of a localized stress by the application of an electric field, each of specimens A, B and C was subjected to Raman microspectroscopy upon application of no electric field (0 kV/cm).

Figure 2:
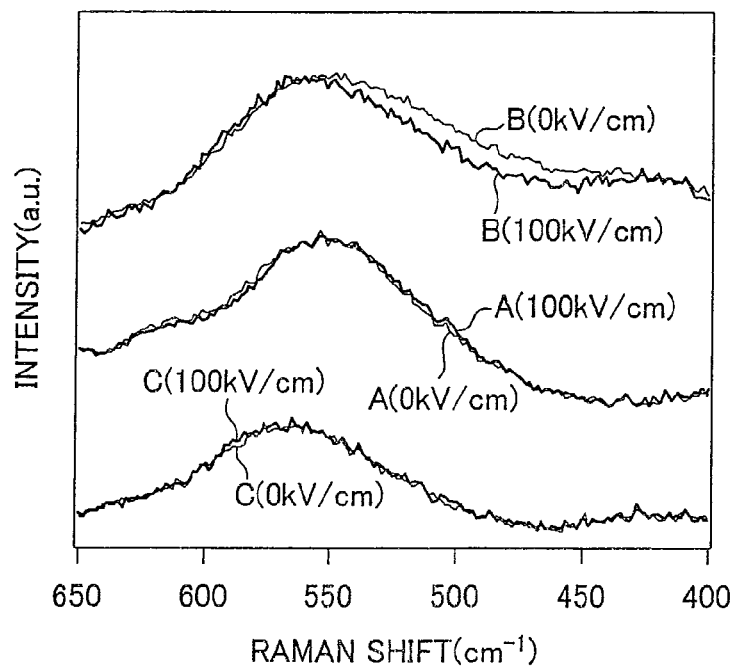
FIG. 2 is a graph showing the Raman spectra of piezoelectric films as measured in Example 1.

FIG. 2 is a graph with the vertical axis representing the intensity and the horizontal axis representing the Raman shift ranging from 650 cm$^{-1}$ to 400 cm$^{-1}$, which shows the Raman spectra of each of specimens A, B and C that were measured upon application of electric fields of 100 kV/cm and 0 kV/cm, respectively. The spectra as shown are those measured at one point for each specimen.

As seen from FIG. 2, in each of specimens A and C, there was little difference between the Raman spectrum in the Raman shift range of 500 to 600 cm$^{-1}$ upon application of an electric field of 0 kV/cm and that upon application of an electric field of 100 kV/cm. On the other hand, in specimen B, the Raman spectrum upon application of an electric field of 100 kV/cm greatly changed from that upon application of an electric field of 0 kV/cm.

The above indicates that stress was small at the measuring points in specimens A and C, while it was large at the measuring point in specimen B.

In other words, when an electric field of 100 kV/cm was applied to the PZT film 12, generation of a large stress was detected in specimen B which had been prepared without annealing and was subjected to the measurement at the points located on the film within 3 μm of the upper electrode, whereas substantially no stress was detected in specimen C which also had been prepared without annealing but was subjected to the measurement at the points located on the film 20 μm away from the upper electrode. It is thus confirmed that the stress generated by applying an electric field to the PZT film 12 is localized.

Figure 3A:
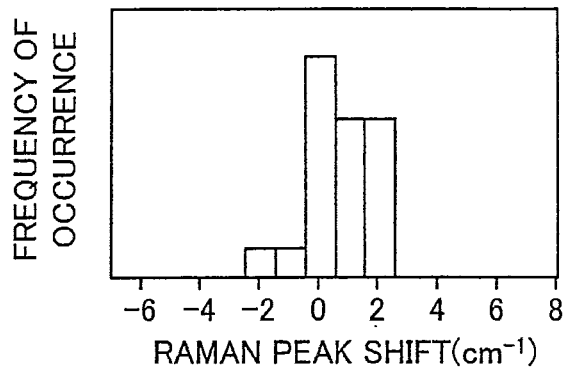
FIG. 3A is a histogram showing the Raman peak shift amounts obtained from an annealed piezoelectric film and their frequencies of occurrence in Example 1.
Figure 3B:
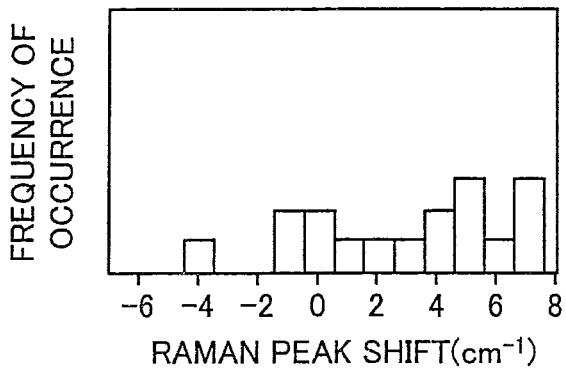
FIG. 3B is a histogram showing the Raman peak shift amounts obtained from a non-annealed piezoelectric film and their frequencies of occurrence in Example 1.

FIGS. 3A and 3B are histograms for specimens A and B, respectively, each showing the Raman peak shift amounts, which were found between the spectra upon application of an electric field of 0 kV/cm and the spectra upon application of an electric field of 100 kV/cm, and their frequencies of occurrence.

As shown in FIG. 3A, the Raman peak shift amounts which were obtained from all the measuring points of specimen A prepared with annealing of the deposited PZT film 12 were 2.0 cm$^{-1}$ or less. In contrast, it is seen from FIG. 3B that the Raman peak shift amounts which were obtained from the measuring points of specimen B prepared without annealing of the deposited PZT film 12 varied widely, with some of them even having been over 2.0 cm$^{-1}$.

The measurement results as shown in FIGS. 2, 3A and 3B indicate that specimen A prepared with annealing had a small (reduced) stress generated therein during the application of an electric field of 100 kV/cm to the PZT film 12 as compared with specimen B prepared without annealing. Consequently, it has been found that the stress localization during the application of an electric power is reduced by annealing the deposited PZT film

[Durability Evaluation at High Humidity]

Durability evaluation was performed on two piezoelectric thin-film devices 14 for which the above specimens A and B were employed, respectively.

Each of the two piezoelectric thin-film devices 14 was placed in an atmosphere at a temperature of 40° C. and a relative humidity of 80%, then an electric field of 60 kV/cm with a trapezoidal waveform and a cycle period of 10 μsec (100 kHz) was continuously applied to the upper electrode 32 as a driving electrode so as to count cycles until the piezoelectric film 12 was broken.

The piezoelectric film 12 was considered to be broken when the dielectric dissipation factor thereof, which had been 1 to 3% before application of the electric field, reached 20% as a result of the increase along with the deterioration of the film 12 caused under the electric field applied thereto by the ion migration of a constituent element of the film 12.

The results are as follows: The PZT film (piezoelectric film) 12 of specimen A, in which the stress localization during the application of an electric field was reduced by annealing the deposited PZT film 12, was broken after 250 billion cycles, while the PZT film 12 of specimen B, in which the stress localization during the application of an electric field was not reduced because the deposited PZT film 12 had not been annealed, was broken after three billion cycles.

It has been confirmed from the above that the relief of a localized stress in the PZT film 12 by the annealing of the deposited film 12 is effective at improving the device durability.

Example 2

A plurality of piezoelectric thin-film devices were fabricated by forming lower electrodes 30 on substrates 28 by sputtering in a similar manner to Example 1, depositing PZT films 12 each having a thickness of 4.0 μm by sputtering under different conditions for film deposition including film deposition temperature and gas pressure, then annealing the films 12, and forming upper electrodes 32 by sputtering.

Electric fields were applied to each piezoelectric thin-film device in a similar manner to Example 1, and the relevant device was subjected to Raman microspectroscopy at the points on the surface of the PZT film (piezoelectric film) 12 that were each within 3 μm of the boundary between the upper electrode 32 and the PZT film 12, and to durability evaluation at high humidity.

Figure 4:
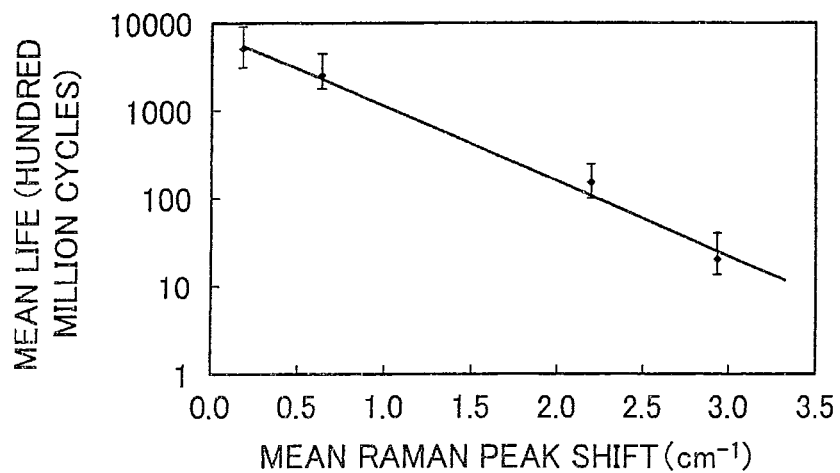
FIG. 4 is a graph showing a correlation between the mean Raman peak shift amount and the mean life with respect to the piezoelectric films formed in Example 2.

FIG. 4 is a graph showing the correlation between the mean Raman peak shift amount (on an absolute-value basis) in the range of 500 to 650 cm$^{-1}$ and the mean life with respect to the PZT films of the specimens, with the values of the mean Raman peak shift amount having been obtained from each specimen by Raman microspectroscopy at a plurality of measuring points (about 20 points).

As seen from FIG. 4, the mean Raman peak shift amount, which is defined as the mean of the absolute values of the Raman peak shift amounts found at a plurality of measuring points on the surface of a piezoelectric film, varied with the conditions for film deposition such as film deposition temperature and gas pressure, which indicates that the localized stress generated in the PZT film 12 during the application of an electric field thereto varies with the conditions for film deposition. It is also indicated that the specimens with varying, localized stresses are very different from one another in durability.

In consequence, it has been found that the mean Raman peak shift amount upon application of an electric field should be made 2.2 cm$^{-1}$ or less in order to achieve a device with a durability lasting for ten billion cycles, which is considered as an index to actual use.

What is claimed is:

1. A perovskite-type oxide film having a perovskite-type crystal structure and containing lead as a chief component, which, when subjected to Raman microspectroscopy at a plurality of points on a surface thereof so as to measure Raman spectra upon application of an electric field of 100 kV/cm and upon application of no electric field, has a mean of absolute values of peak shift amounts that is 2.2 cm$^{-1}$ or less, with the peak shift amounts being found between Raman spectra in a range of 500 to 650 cm$^{-1}$ measured upon application of an electric field of 100 kV/cm and Raman spectra in the range of 500 to 650 cm$^{-1}$ measured upon application of no electric field.

2. The perovskite-type oxide film according to claim 1, wherein each of said points, at which said Raman spectra are measured, is located within 3 μm of an upper electrode.

3. The perovskite-type oxide film according to claim 1, wherein said oxide film is a lead zirconate titanate film.

4. The perovskite-type oxide film according to claim 1, wherein said oxide film is a lead zirconate titanate film containing at least one metal element selected from the group consisting of niobium (Nb), bismuth (Bi), strontium (Sr), barium (Ba), calcium (Ca), and lanthanum (La).

5. The perovskite-type oxide film according to claim 1, wherein said oxide film is deposited by sputtering.

6. The perovskite-type oxide film according to claim 5, wherein said oxide film is annealed after being deposited by sputtering.

7. The perovskite-type oxide film according to claim 6, wherein said oxide film is annealed at a temperature of 150 to 500° C. for two to ten hours.

8. A piezoelectric thin-film device comprising:
   a piezoelectric film composed of the perovskite-type oxide film according to claim 1; and
   a lower electrode and an upper electrode formed on two surfaces of the piezoelectric film, respectively, to apply a voltage to the piezoelectric film.

9. The piezoelectric thin-film device according to claim 8, wherein said piezoelectric film has a lead concentration near an interface with said lower electrode which is equal to or higher than a mean lead concentration of said piezoelectric film as a whole.

10. A liquid ejection unit comprising:
    a liquid storing/ejecting member provided with a liquid reservoir for storing liquid and a liquid ejecting port connecting the liquid reservoir with outside; and
    the piezoelectric thin-film device according to claim 8 which is so arranged as to face the liquid reservoir.

11. A process for producing a perovskite-type oxide film, comprising the steps of:
    depositing a perovskite-type oxide film having a perovskeite-type crystal structure and containing lead as a chief component by sputtering;
    annealing the oxide film deposited at a specified temperature for a specified period of time;
    subjecting the oxide film after annealing to Raman microspectroscopy at a plurality of points on a surface thereof so as to measure Raman spectra upon application of an electric field of 100 kV/cm and upon application of no electric field;
    finding conditions under which a mean of absolute values of peak shift amounts is 2.2 cm$^{-1}$ or less, with the peak shift amounts being found between Raman spectra in a range of 500 to 650 cm$^{-1}$ measured upon application of an electric field of 100 kV/cm and Raman spectra in the range of 500 to 650 cm$^{-1}$ measured upon application of no electric field; and
    producing the perovskite-type oxide film under the conditions found.

12. The process for producing a perovskite-type oxide film according to claim 11, wherein said mean of the absolute values of the peak shift amounts is used for durability evaluation, and said perovskite-type oxide film is produced when evaluated as durable.

13. The process for producing a perovskite-type oxide film according to claim 11, wherein said step of annealing is performed at a temperature of 150 to 500° C. for two to ten hours.

14. A method of evaluating a perovskite-type oxide film, comprising the steps of:
    subjecting a perovskite-type oxide film having a perovskeite-type crystal structure and containing lead as a chief component to Raman microspectroscopy at a plurality of points thereon so as to measure Raman spectra upon application of an electric field of 100 kV/cm and upon application of no electric field;
    determining whether or not a mean of absolute values of peak shift amounts is 2.2 cm$^{-1}$ or less, with the peak shift amounts being found between Raman spectra in a range of 500 to 650 cm$^{-1}$ measured upon application of an electric field of 100 kV/cm and Raman spectra in the range of 500 to 650 cm$^{-1}$ measured upon application of no electric field; and
    evaluating the perovskite-type oxide film as capable of relieving stress localized during application of an electric field to the film if the mean of the absolute values of the peak shift amounts is 2.2 cm$^{-1}$ or less.

15. The method of evaluating a perovskite-type oxide film according to claim 14, wherein said oxide film is evaluated as adequately durable if said mean of the absolute values of the peak shift amounts is 2.2 cm$^{-1}$ or less.

* * * * *